United States Patent [19]

Stec et al.

[11] Patent Number: 4,684,742
[45] Date of Patent: Aug. 4, 1987

[54] PROCESS FOR THE PRODUCTION OF 2-(2-HALOGENOETHYLAMINO)-2-OXO-3-(2-HALOGENOETHYL)-1.3.2.-OXAZAPHOSPHORINANES

[75] Inventors: Wojciech Stec, Falista; Ryszard Kinas, Maratonska; Konrad Misiura, Marysinska, all of Poland

[73] Assignee: Polska Akademia Nauk-Centrum Baden Molekularnych i Makromolekularnych, Lodz, Poland

[21] Appl. No.: 758,484

[22] Filed: Jul. 24, 1985

[30] Foreign Application Priority Data

Jul. 31, 1984 [PL] Poland .................................. 249007

[51] Int. Cl.$^4$ ............................................. C07F 9/21
[52] U.S. Cl. ..................................................... 558/81
[58] Field of Search .................................. 558/144, 81

[56] References Cited

FOREIGN PATENT DOCUMENTS 1190054 7/1970 United Kingdom .

OTHER PUBLICATIONS

Asta-Werke, "Chem. Abstracts", vol. 71, (1969), 49998m, Abstract of French Pat. No. 1,530,962, 6/28/68.
Lassauniere et al, "Chem. Abstracts", vol. 71, (1969), 30585c, Abstract of French Pat. No. 1,537,175, 8/23/68.

*Primary Examiner*—Anton H. Sutto
*Attorney, Agent, or Firm*—Ladas & Parry

[57] ABSTRACT

Process for production of racemic or enantiomeric form of 2-(2-halogenoethylamino)-2-oxo-3-(2-halogenoethyl)-1.3.2.-oxazaphosphorinanes of general formula 1,

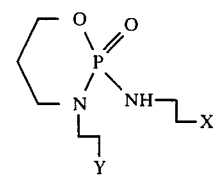

form. 1 wherein X and Y are the same or different and represent halogen atoms is based, according to invention, on the reaction of enantiomeric or racemic form of ethyleneimide of general formula 2,

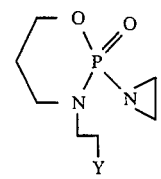

form. 2 wherein Y is the same as above, with aqueous solution of hydrogen halide. Compounds of general formula 1, where X and Y are different and represent halogen atoms, possess better antileukemic activity than ifosfamide.

9 Claims, No Drawings

PROCESS FOR THE PRODUCTION OF 2-(2-HALOGENOETHYLAMINO)-2-OXO-3-(2-HALOGENOETHYL)-1.3.2.-OXAZAPHOSPHORINANES

The present invention is related to the production of 2-(2-halogenoethylamino)-2-oxo-3-(2-halogenoethyl)-1.3.2-oxazaphosphorinanes in the form of racemic mixtures or individual enantiomers of general formula 1, wherein X and Y are both the same or different and represent halogen atoms. These compounds possess anticancer activity. Compound of general structure 1, wherein X and Y represent chlorine atom is known and clinically used as antitumor drug under trade name Holoxan or Ifosfamide.

From the French Pat. No. 1530962 description there is known the method of preparation of compounds of general structure 1, which is based on the ethyleneimide ring opening by means of dry hydrogen halide. French Patent emphasized that ring opening has to be performed substantially in the absence of water although desired products are obtainable too, in the presence of only traces of water.

It was found, unexpectedly, that ethyleneimide ring opening process can be performed by means of aqueous solutions of hydrogen halide and the product of general structure 1, where X and Y are as above, is available in the yield 75–80% while the yield claimed in the French Pat. No. 1530962 for ring opening under non-aquous conditions was 63.6%.

The procedure of preparation of compounds of general structure 1, according to our invention has this distinction from the so far presented methods that racemic or enantiomeric ethyleneimide of structure 2, wherein Y has meaning as above, is treated with aqueous solution of hydrogen halide. The procedure of preparation according to our invention is illustrated in the enclosed Scheme. In the formula HX, what means hydrogen halide, X has a meaning as above.

The compound of general structure 2, being a substrate for reaction with HX, where HX has a meaning as above, can be dissolved in water, in the mixture of water-organic solvent, or in organic solvent.

Compounds obtained according to the procedure presented in our invention, of general formula 1, are extracted from water solutions with organic solvents and then are purified by means of cristallization or column chromatography. It was found unexpectedly, that treatment of compounds of general formula 2 with aquous hydrogen halide solutions does not cause of the cleavage of any P-N bond and the yields of products are higher than presented within French Pat. No. 1530962. Furthermore, aquous solutions of HX, where X has a meaning as above, do not cause racemization of optically active compounds of general formula 1 or 2. Compounds of general formula 1, wherein both substituents X and Y are bromine atoms, or one of them is chlorine while another one is bromine, which were not so far characterized in the literature by means of their physicochemical parameters, have shown better antitumor activity than parent ifosfamide (Holoxan), compound of structure 1 wherein both X and Y are chlorine atoms. The data concerning antitumor activity of compounds of general structure 1, wherein at least one X or Y substituent is bromine, are collected in Table 1.

TABLE 1

Antileukemic activity against L1210, toxicity and therapeutic indexes of compounds of general structure 1.

| Compound 1 | | $ED_{50}$ | $LD_{50}$ | Therapeutic |
|---|---|---|---|---|
| X | Y | mg/kg | mg/kg | index |
| Cl | Br | 44 | 512 | 11.6 |
| Br | Cl | 38 | 334 | 8.8 |
| Br | Br | 43 | 459 | 10.7 |
| Br | Cl* | 30 | 367 | 12.2 |
| Cl | Cl | 103 | 680 | 6.6 |

Antileukemic activity was evaluated in L1210 leukemic CD2F$_1$ female mice ED$_{50}$ doses producing the 50% increase in life span of treated mice over control were estimated from experimental data by regression anlysis. Toxicity (LD$_{50}$) were determined in healthy CD2F$_1$ female mice during 14 days observation period. TI = LD$_{50}$/ED$_{50}$
*Optically active levorotatory compound, $|\alpha|_D^{20} = -41.7°$ (c 3.0, MeOH).

The more advantageous than parent ifosfamide appeared to be: 2-(2-bromoethylamino)-2-oxo-3-(2-chloroethyl)-1.3.2-oxazaphosphorinane, 2-(2-bromoethylamino)-2-oxo-3-(2-bromoethyl)-1.3.2-oxazaphosphorinane and 2-(2-chloroethylamino)-2-oxo-3-(2-bromoethyl)-1.3.2-oxazaphosphorinane as racemic or enantiomeric compounds.

It compared with known procedures, that one being a matter of our invention has the substantial advantage that in can be performed in aquous medium what eliminates the use of expensive neutral organic solvents necessary for the formation of saturated hydrogen halide solutions.

The following examples serve to further illustrate the presented invention.

EXAMPLE I 2-(2-bromoethylamino(-2-oxo-3-(2-chloroethyl)-1.3.2-oxazaphosphorinane Into the solution of 2-ethyleneimine-2-oxo-3-(2-chloroethyl)-1.3.2-oxazaphosphorinane (1.12 g, 5.0 mM) in chloroform (10 mL) was added dropwise with stirring, 6% aq. solution of hydrobromic acid (6.55 mL, 5.0 mM). Stirring at room temperature was continued for 15 min. Organic fraction was separated and aquous layer was extracted with chloroform (2×5 mL). Organic fractions were combined together, dried over anhydrous MgSO$_4$ and concentrated under reduced pressure. Crude product was crystallized from ether-n-pentane to give 1.17 g of crystalline product (77% of theoretical yield), mp. 59°–60° C., $\delta_{31P}$ 11.4 ppm (CHCl$_3$); Mass spectrum m/e: 308 (0.4%), 306 (1.6%), 304 (1.1%), 255 (100%), 257 (95%).

EXAMPLE II 2-(2-bromoethylamino)-2-oxo-3-(2-chloroethyl)-1.3.2-oxazaphosphorinane Into the solution of 2-ethyleneimine-2-oxo-3-(2-chloroethyl)-1.3.2-oxazaphosphorinane (1.68 g, 7.5 mM) in the water (30 mL) was added, with stirring, 6% aq. solution of hydrogen bromide (9.83 mL, 7.5 mM). Stirring at room temperature was continued for further 15 min and then reaction mixture was extracted with chloroform (3×10 mL). Extracts were combined together, dried over anhydrous MgSO$_4$ and concentrated under reduced pressure. Residual material was loaded on silica gel column (15 g, Kieselgel 60, 70–230 mesh) and eluted with chloroform-ethanol (9:1). 1.65 g (72%) of crystalline product was obtained, which after crystallization from ether-n-pentane had mp. 59°–60° C. $\delta_{31P}$=11.4 ppm (CHCl$_3$); R$_f$=0.44

(CHCl₃:EtOH=9:1); mass spectrum as described in example I.

EXAMPLE III (−)-S-2-(2-bromoethylamino)-2-oxo-3-(2-chloroethyl)-1.3.2-oxazaphosphorinane Into the solution of (−)-S-2-ethyleneimino-2-oxo-3-(2-chloroethyl)-1.3.2-oxazaphosphorinane (1.12 g, 5.0 mM; $|\alpha|_D^{20} = -25.8°$ (c 3.0, MeOH) in chloroform (10 mL) was added dropwise, with stirring 6% aq. solution of hydrobromic acid (6.55 mL, 5.0 mM). Stirring was continued for 15 min and chloroform layer was separated. Aquous layer was extracted with chloroform (2×5 mL) and combined chloroform layers were combined together and dried over anhydrous MgSO₄. Removal of solvent under reduced pressure left the crystalline product which after crystallization from ether-n-pentane had mp. 88°90° C. Yield 1.23 g (81%), $\delta_{31P} = 11.4$ ppm (CHCl₃); $|\alpha|_D^{20} = -41.7°$ (c. 3.0, MeOH). Mass spectrum as described in example I.

EXAMPLE IV (+)-R-2-(2-Bromoethylamino)-2-oxo-(2-chloroethyl)-1.3.2-oxazaphosphorinane Starting from (+)-R-2-ethyleneimino-2-oxo-3-(2-chloroethyl)-1.3.2-oxazaphosphorinane $|\alpha|_D^{20} = +26.2°$ in a way analogous to that presented in example III dextrarotatory product was obtained in 80% yield; $|\alpha|_D^{20} + 42.1°$ (c 3.4, MeOH).

EXAMPLE V 2-(2-chloroethylamino)-2-oxo-3-(2-chloroethyl)-1.3.2-oxazaphosphorinane Into the stirred solution of 2-ethyleneimino-2-oxo-3-(2-chloroethyl)-1.3.2-oxazaphosphorinane (1.12 g, 5.0 mM) in chloroform (12 ml) was added at room temperature dropwise 3% aq. solution of hydrogen chloride (6 mL, 5.0 mM). Stirring was continued for 15 min, organic layer separated and aquous layer extracted with chloroform (2×6 mL). Organic layers were combined together, dried over anhydrous MgSO₄. Removal of solvent under reduced pressure left a residue which upon crystallization from ether-n-pentane gave 1.02 g of crystalline product, mp. 45°-46° C. in 78% yield. $\delta_{31P} = 11.3$ ppm (CHCl₃). Mass spectrum m/e: 262 (0.3%), 260 (0.3%), 260 (0.8%), 213 (37%), 211 (100%).

EXAMPLE VI 2-(2-Bromoethylamino)-2-oxo-3-(2-bromoethyl)-1.3.2-oxazaphosphorinane Into the stirred solution of 2-ethyleneimino-2-oxo-3-(2-bromoethyl)-1.3.2-oxazaphosphorinane (1.35 g, 5.0 mM) in chloroform (10 mL) was added dropwise, at room temperature during 15 min 6% aq. hydrogen bromide. Chloroform layer was separated and water layer was exacted with chloroform (2×5 mL). Organic layers were combined together, dried over anhydrous MgSO₄ and concentrated under reduced pressure. Raw product was crystallized from ether-n-pentane. 1.31 g of crystalline product was obtained in 75% yield, mp. 58°-59° C. $\delta_{31P} = 11.2$ ppm (CHCl₃), mass spectrum m/e: 352 (0.7%), 350 (1.1%), 348 (0.6%), 255 (100%), 257 (98%).

EXAMPLE VII 2-(2-Chloroethylamino)-2-oxo-3-(2-bromoethyl)-1.3.2-oxazaphosphorinane.

Into the stirred solution of 2-ethyleneimino-2-oxo-3-(2-bromoethyl)-1.3.2-oxazaphosphorinane (1.35 g, 5.0 mM) in chloroform (10 mL) was added dropwise at room temperature 3% aq. solution of hydrogen chloride (6.0 mL, 5.0 mM). Stirring was continued for 15 min. Organic phase was separated and equeous layer was extracted with chloroform (2×6 mL). Organic layers were combined together, dried over anhydrous MgSO₄ and concentrated under reduced pressure. Raw product was purified on Silicagel column (Silicagel 230–400 mesh, chloroform-acetone (1:1)) and crystallized from ether-n-pentane. 1.13 g of white, crystalline product was obtained (yield 74.5%) mp. 50°-51° C., $\delta_{31P} = 11.6$ ppm (CHCl₃). Mass spectrum m/e: 308 (0.2%), 306 (0.96%), 304 (0.7%), 211 (100%), 213 (33%).

What we claim is:

1. A process for the preparation of racemic or enantiomeric forms of 2-(2-halogenoethylamino)-2-oxo-3-(2-halogenoethyl)-1.3.2.-oxazaphosphorinanes of general formula 1,

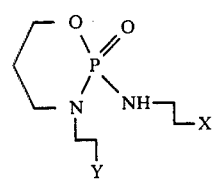

form. 1 wherein X and Y are the same or different and represent halogen atoms, which comprises reacting an aqueous solution containing 3–6% hydrogen halide with racemic or enantiomeric ethyleneimide of general formula 2,

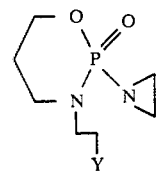

form. 2 wherein Y is as defined above, dissolved in water or in chloroform.

2. A process as claimed in claim 1 wherein racemic or enantiomeric form of 2-ethyleneimino-2-oxo-3-(2-chloroethyl)-1.3.2-oxazaphosphorinane dissolved in water or in chloroform is reacted with an aqueous solution containing 3–6% hydrogen bromide to produce racemic or enantiomeric 2-(2-bromoethylamino)-2-oxo-3-(2-chloroethyl)-1.3.2.-oxazaphosphorinane.

3. A process as claimed in claim 1 wherein racemic or enantiomeric form of 2-ethyleneimino-2-oxo-3-(2-bromoethyl)-1.3.2-oxazaphosphorinane dissolved in water or in chloroform is reacted with aqueous solution containing 3–6% hydrogen bromide to produce racemic or enantiomeric 2-(2-bromoethylamino)-2-oxo-3-(2-bromoethyl)-1.3.2.-oxazaphosphorinane.

4. A process as claimed in claim 1 wherein racemic or enantiomeric form of 2-ethyleneimino-2-oxo-3-(2-bromoethyl)-1.3.2-oxazaphosphorinane dissolved in water or in chloroform is reacted with aqueous solution containing 3–6% hydrochloric acid to produce racemic or enantiomeric 2-(2-chloroethylamino)-2-oxo-3-(2-bromoethyl)-1.3.2.-oxazaphosphorinane.

5. A process as in claim 1 wherein said aqueous solution of hydrogen halide comprises 6% hydrogen halide.

6. A process as in claim 1 wherein said hydrogen halide comprises hydrogen bromide.

7. A process as in claim 5 wherein said hydrogen halide comprises hydrogen bromide.

8. A process as in claim 5 wherein said compound of formula 2 is dissolved in chloroform.

9. A process as in claim 1 wherein said compound of formula 2 is dissolved in chloroform.

* * * * *